US008975274B2

(12) United States Patent
Gribble et al.

(10) Patent No.: US 8,975,274 B2
(45) Date of Patent: *Mar. 10, 2015

(54) COMPOSITIONS AND METHODS FOR TREATING CANCER

(71) Applicant: Trustees of Dartmouth College, Hanover, NH (US)

(72) Inventors: Gordon W. Gribble, Lebanon, NH (US); Justin M. Lopchuk, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/345,728

(22) PCT Filed: Sep. 18, 2012

(86) PCT No.: PCT/US2012/055847
§ 371 (c)(1),
(2) Date: Mar. 19, 2014

(87) PCT Pub. No.: WO2013/043558
PCT Pub. Date: Mar. 28, 2013

(65) Prior Publication Data
US 2014/0228392 A1    Aug. 14, 2014

Related U.S. Application Data

(63) Continuation of application No. 13/236,969, filed on Sep. 20, 2011, now Pat. No. 8,530,496.

(51) Int. Cl.
*A61K 31/473* (2006.01)
*A61K 31/4709* (2006.01)
*C07D 401/12* (2006.01)
*C07D 219/10* (2006.01)
*C12N 5/09* (2010.01)

(52) U.S. Cl.
CPC ............ *C07D 401/12* (2013.01); *C07D 219/10* (2013.01); *C12N 5/0693* (2013.01); *A61K 31/473* (2013.01)
USPC .......................................... 514/297; 514/313

(58) Field of Classification Search
USPC ................................................. 514/297, 313
See application file for complete search history.

(56) References Cited

U.S. PATENT DOCUMENTS

| 2,113,357 | A | 4/1938 | Mietzsch et al. ............... 546/106 |
| 2,441,665 | A | 5/1948 | Holcomb et al. ............... 546/106 |
| 2,503,889 | A | 4/1950 | Silven et al. ..................... 451/25 |
| 5,886,185 | A | 3/1999 | Chou et al. .................... 546/106 |
| 6,187,787 | B1 | 2/2001 | Gribble et al. ................. 514/297 |
| 7,135,494 | B2 | 11/2006 | Munro et al. .................. 514/411 |
| 7,919,500 | B2 | 4/2011 | Gribble et al. ................. 514/285 |
| 8,518,965 | B2 | 8/2013 | Gribble et al. ................. 514/297 |
| 8,530,496 | B2 * | 9/2013 | Gribble et al. ................. 514/297 |
| 2006/0088934 | A1 | 4/2006 | Greene et al. .................. 435/368 |
| 2009/0176745 | A1 | 7/2009 | Arbiser ......................... 514/114 |
| 2011/0118296 | A1 | 5/2011 | Gribble et al. ................. 514/285 |

FOREIGN PATENT DOCUMENTS

| JP | 08044114 A | 2/1996 |
| WO | WO 2011/016952 A1 | 2/2011 |

OTHER PUBLICATIONS

Awada et al. "Clinical Phase I and Pharmacokinetic Study of S 16020, a New Olivacine Derivative: Report on Three Infusion Schedules" Annals of Oncology 2002 13(12):1925-1934.
Barbet et al. "DNA Polyintercalating Drugs. Proton Magnetic Resonance Studies of a New Acridine Dimer. Conformations and Interactions with Mono- and Dinucleotides" Biochemistry 1976 15(12):2642-2650.
Becker, M.M. and Dervan, P.B. "Molecular Recognition of Nucleic Acid by Small Molecules. Binding Affinity and Structural Specificity of Bis(methidium)spermine" Journal of the American Chemical Society 1979 101(13):3664-3666.
Canellakis et al. "Diacridines: Bifunctional Intercalators I.Chemistry, Physical Chemistry and Growth Inhibitory Properties" Biochimica et Biophysica Acta 1976 418:277-289.
Capelle et al. "Deoxyribonucleic Acid Bifunctional Intercalators: Kinetic Investigation of the Binding of Several Acridine Dimers to Deoxyribonucleic Acid" Biochemistry 1979 18(15):3354-3362.
Denny et al. "Potential Antitumor Agents. 44. Synthesis and Antitumor Activity of New Classes of Diacridine: Importance of Linker Chain Rigidity for DNA Binding Kinetics and Biological Activity" Journal of Medicinal Chemistry 1985 28:1568-1574.
Feigon et al. "Interactions of Antitumor Drugs with Natural DNA: $^1$H NMR Study of Binding Mode and Kinetics" Journal of Medicinal Chemistry 1984 27:450-465.
Gourdie et al. "Synthesis and Evaluation of DNA-Targeted Spatially Separated Bis(aniline mustards) as Potential Alkylating Agents with Enhanced DNA Cross-Linking Capability" Journal of Medicinal Chemistry 1991 34(1):240-248.
Jaycox et al. "Potential DNA bis-Intercalating Agents: Synthesis and Antitumor Activity of Novel, Conformationally Restricted bis(9-Aminoacridines)" Journal of Heterocyclic Chemistry 1987 vol. 24:1405-1408.
Le Pecq et al. "DNA Polyintercalating Drugs: DNA Binding of Diacridine Derivatives" Proceedings of the National Academy of Science USA 1975 72(8):2915-2919.
Mayer, A.M.S. and Gustafson, K.R. "Marine Pharmacology in 2001-2: Antitumour and Cytotoxic Compounds" European Journal of Cancer 2004 40(18):2676-2704.
Nagesh, N. and Krishnaiah, A. "A Comparative Study on the Interaction of Acridine and Synthetic *bis*-acridine with G-quadruplex Structure" Journal of Biochemical and Biophysical Methods 2003 57:65-74.

(Continued)

*Primary Examiner* — Charanjit Aulakh
(74) *Attorney, Agent, or Firm* — Licata & Tyrell P.C.

(57) ABSTRACT

The present invention is bis-acridine or bis-quinoline intercalators having a modified bis(4-aminophenyl)ether tether to improve activity, selectivity, solubility and bioavailability of the antitumor compound.

2 Claims, No Drawings

(56) References Cited

OTHER PUBLICATIONS

Palit et al. "Phase Transfer Catalyzed Synthesis of bis-quinolines: Antileishmanial Activity in Experimental Visceral Leishmaniasis and in vitro Antibacterial Evaluation" European Journal of Medicinal Chemistry 2009 44:845-853.

Šebestík et al. "Solid-phase Synthesis of Head and Tail bis-acridinylated Peptides" Tetrahedron Letters 2004 45:1203-1205.

Strekowski et al. "Bis-4-aminoquinolines: Novel Triple-Helix DNA Intercalators and Antagonists of Immunostimulatory CpG-Oligodeoxynucleotides" Bioorganic & Medicinal Chemistry 2003 11:1079-1085.

Urban et al. "Coproverdine, a Novel, Cytotoxic Marine Alkaloid from a New Zealand Ascidian" Journal of Natural Products 2002 65(9):1371-1373.

Wakelin et al. "Structural Limitations on the Bifunctional Intercalation of Diacridines into DNA" Biochemistry 1978 17(23):5057-5063.

Wakelin, L.P.G. "Polyfunctional DNA Intercalating Agents" Medicinal Research Reviews 1986 6(3):275-340.

Wang et al. "Linker-modified Triamine-linked Acridine Dimers: Synthesis and Cytotoxicity Properties in vitro and in vivo" Bioorganic & Medicinal Chemistry 2007 15:735-748.

Xu et al. "A High-content Chemical Screen Identifies Ellipticine as a Modulator of p53 Nuclear Localization" Apoptosis 2008 13(3):413-422.

Zhang, A. and Guogiang, L. "The First Synthesis of Clausenamine-A and Cytotoxic Activities of Three Biscarbazole Analogues Against Cancer Cells" Bioorganic & Medicinal Chemistry Letters 2000 10:1021-1023.

International Search Report from PCT/US09/49560, Aug. 27, 2009.
International Search Report from PCT/US10/41784, Sep. 9, 2010.
International Search Report from PCT/US12/55847, Nov. 20, 2012.
International Preliminary Report on Patentability from PCT/US12/55847, Apr. 3, 2014.

* cited by examiner

COMPOSITIONS AND METHODS FOR TREATING CANCER

This application is the national stage under 35 U.S.C. §371 of PCT International Application No. PCT/US2012/055847, filed Sep. 18, 2012, which claims the benefit of priority of U.S. application Ser. No. 13/236,969 filed Sep. 20, 2011, the contents of which are incorporated herein by reference in their entirety.

BACKGROUND OF THE INVENTION

Intercalation is one of several modes by which drugs interact with DNA wherein a planar portion of the drug is inserted in between adjacent stacked base pairs of a double stranded DNA. The intercalation process results in helix extension and unwinding of the DNA. Included within these drugs are antitumor agents, actinomycin D, adriamycin and daunomycin, as well as several drugs for treatment of parasitic disease including ethidium bromide, quinacrine, chloroquine and miracil D. U.S. Pat. No. 2,441,665 discloses a class of alkylene diamine derivatives which are valuable as antimalarial agents. U.S. Pat. No. 2,113,357 discloses substituted aminoacridine derivatives useful in treating blood parasites.

DNA intercalating ligands have also been shown to be useful in targeting alkylating agents to DNA by attachment of the intercalating ligand to the alkylating agent (Gourdie, et al. (1991) *J. Med. Chem.* 34:240-248). Since the biological properties of these DNA intercalating drugs are believed to result from their binding, research efforts have focused on designing molecules that have a high affinity for DNA. Planar polycyclic aromatic molecules show a strong propensity to bind to DNA by intercalation (Jaycox, et al. (1987) *J. Heterocyclic Chem.* 24:1405-1408; U.S. Pat. No. 6,187,787). In this respect, efforts to identify molecules with a greater affinity and selectivity for DNA have resulted in the development of bifunctional intercalating agents in which two intercalating ligands are bridged by a central linking chain. In general, enhanced binding is observed with molecules of this type (Canellakis, et al. (1976) *Biochim. Biophys. Acta* 418:277; Becker & Dervan (1979) *J. Am. Chem. Soc.* 101:3664; Wakelin, et al. (1986) *Med. Res. Rev.* 6:275).

A homologous series of bisacridines containing two 9-aminoacridine chromophores linked via a simple methylene chain has been studied to investigate the minimum interchromophore separation required to permit bifunctional intercalation (Wakelin, et al. (1978) *Biochemistry* 17:5057). Viscometric, sedimentation and electric dichroism experiments showed that compounds having one to four methylene groups in the linker are restricted to monofunctional intercalation whereas bifunctional interaction was observed when the chain length was increased to six methylene groups or more.

Additional studies indicate that the nature of the bridging chain and/or substituents on the acridine ring has a profound effect on the ability of bisacridine compounds to act as bifunctional intercalating agents. DNA binding characteristics of a number of acridine dimers of which two aromatic rings, each ring being the monomeric 2-methoxy-6-chloro-9-(3-dimethyl amino propylamino acridine), were linked by a chain of varying length and structure were also determined (Le Pecq, et al. (1975) *Proc. Nat'l Acad. Sci. USA* 72(8): 2915-2919). The linking chains of these acridine dimers included —(CH$_2$)$_3$—NH—(CH$_2$)$_4$—NH—(CH$_2$)$_3$—; —(CH$_2$)$_3$—NH—(CH$_2$)$_4$—; and —(CH$_2$)$_3$—NH— (CH$_2$)$_3$—. It was found that the two dimers with the longest chain length bis-intercalated, while only one of the two rings of the dimer with the shortest chain was intercalated. In contrast, bis-intercalators bridged by flexible chains have generally exhibited reduced affinities for DNA, in part because of self-stacking interactions, which compete with the binding process (Barbet, et al. (1976) *Biochemistry* 15:2642; Capelle, et al. (1979) *Biochemistry* 18:3354). Further, bis-intercalation can introduce undesirable entropic effects when a flexible linker is forced into an extended chain conformation (Jaycox et al. (1987) supra). In addition, it is a concern that flexible bis-intercalators can creep in a step-wise fashion along the DNA macromolecule, thereby lowering ligand residence lifetimes at any one site (Denny, et al. (1985) *J. Med. Chem.* 28:1568). Such a process could have significant effects on efficacy of these intercalators as anticancer agents as residence lifetimes have been correlated with in vivo antitumor activity for a large number of DNA intercalators (Feigon, et al. (1984) *J. Med. Chem.* 27:450).

SUMMARY OF THE INVENTION

The present invention features a compound of Formula I, or a pharmaceutically acceptable salt and solvate thereof,

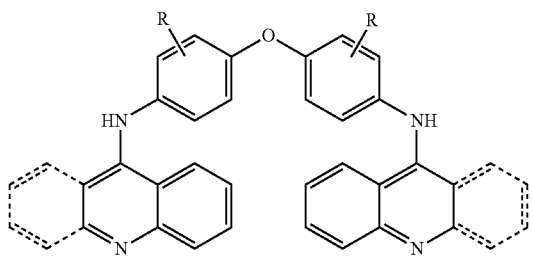

Formula I wherein dashed lines represent bonds that are independently present or absent; and each R is independently an amide, amino, azido, nitro, hydroxyl, hydroxymethyl, carboxyl, cyano, sulfinyl, aryl, heteroaryl, alkenyl, alkyl, alkylene, cycloalkyl, cycloalkenyl, heterocycle, spirocycle, alkoxy, or halo group.

Pharmaceutical compositions and methods of inhibiting cancer cell growth and treating cancer in a subject using a compound of the invention are also provided.

DETAILED DESCRIPTION OF THE INVENTion

The present invention features anti-cancer compounds, pharmaceutical compositions and methods for decreasing tumor cell proliferation, increasing survival, and treating cancer. Specifically, bis-acridine or bis-quinoline intercalators having a modified bis(4-aminophenyl)ether tether have now been developed to improve activity, selectivity, solubility and bioavailability of the antitumor compound. Compounds of the invention find application in decreasing cancer cell proliferation thereby making them useful in the treatment of cancer.

Compounds of the present invention are represented by Formula I:

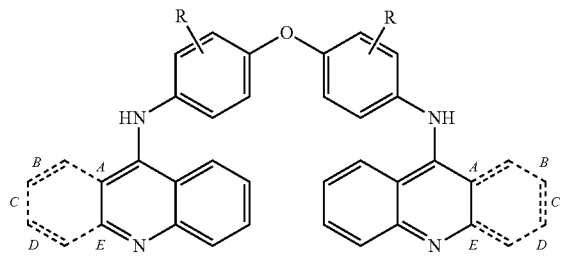

Formula I and include pharmaceutically acceptable salts and solvates thereof. In accordance with Formula I, dashed lines represent bonds (A-E) that are independently present or absent; and R is a group that improves one or more of the pharmacological properties of the drug, e.g., solubility, permeability, bioavailability, stability, pKa, lipophilicity, blood brain barrier penetration, excretion, absorption, distribution, metabolism, transport, clearance, half-life, etc. In certain embodiments, R is an ionizable group, polar group or group capable of participating in H-bonding. In particular embodiments, each R is independently an amide (—$CONH_2$), amino (—$NH_2$), azido (—$N_3$), nitro (—$NO_2$), hydroxyl (—OH), hydroxymethyl (—$CH_2OH$), carboxyl (—$CO_2H$), cyano (—C≡N), sulfinyl (—SO), aryl, heteroaryl, alkenyl, alkyl, alkylene, cycloalkyl, cycloalkenyl, heterocycle, spirocycle, alkoxy, or halo (—Br, —F, —Cl, —I) group.

As used herein, the term "aryl" refers to an optionally substituted benzene ring or to an optionally substituted fused benzene ring system, for example anthracene, phenanthrene, or naphthalene ring systems. Multiple degrees of substitution are included within the present definition. Examples of "aryl" groups include, but are not limited to, phenyl, 2-naphthyl, 1-naphthyl, and the like, as well as substituted derivatives thereof.

As used herein, the term "heteroaryl" refers to an optionally substituted monocyclic five to seven membered aromatic ring, or to an optionally substituted fused bicyclic aromatic ring system comprising two of such aromatic rings. These heteroaryl rings contain one or more heteroatoms such as nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidazolyl, imidazopyridinyl, pyrazolopyridinyl, pyrazolopyrimidinyl, and the like, as well as substituted versions thereof.

As used herein, the term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl, allyl, and the like, as well as substituted versions thereof.

As used herein, the term "alkyl" refers to a straight or branched chain hydrocarbon, preferably having from one to twelve carbon atoms, which may be optionally substituted, with multiple degrees of substitution included within the present invention. Examples of "alkyl" as used herein include, but are not limited to, methyl, ethyl, propyl, isopropyl, isobutyl, n-butyl, isopentyl, n-pentyl, and the like, as well as substituted versions thereof.

As used herein, the term "alkylene" refers to a straight or branched chain divalent hydrocarbon radical, preferably having from one to ten carbon atoms. Alkylene groups as defined herein may optionally be substituted, with multiple degrees of substitution included within the present invention. Examples of "alkylene" as used herein include, but are not limited to, methylene, ethylene, n-propylene, n-butylene, and the like, as well as substituted versions thereof.

As used herein, the term "cycloalkyl" refers to an optionally substituted non-aromatic cyclic hydrocarbon ring, which optionally includes an alkylene linker through which the cycloalkyl may be attached, with multiple degrees of substitution included within the present invention. Exemplary "cycloalkyl" groups include, but are not limited to, cyclopropyl, cyclobutyl, cyclopentyl, cyclohexyl, cycloheptyl, and the like, as well as substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached, with multiple degrees of substitution included within the present invention. Exemplary "cycloalkenyl" groups include, but are not limited to, cyclopropenyl, cyclobutenyl, cyclopentenyl, cyclohexenyl, cycloheptenyl, and the like, as well as substituted versions thereof.

As used herein, the term "heterocycle" or "heterocyclyl" refers to an optionally substituted mono- or polycyclic ring system optionally containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Multiple degrees of substitution are included within the present definition. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

The term "spirocyclyl," as used herein, refers to an alkylene diradical, each end of which is attached to the same carbon atom of the parent molecular moiety forming a bicyclic moiety.

As used herein, the term "alkoxy" refers to the group —$OR^a$, where $R^a$ is alkyl as defined above.

As used herein, the phrase "optionally substituted" or variations thereof denote an optional substitution, including multiple degrees of substitution, with one or more substituent group. Exemplary optional substituent groups include acyl; alkyl; alkenyl; alkynyl; alkylsulfonyl; alkoxy; alkoxycarbonyl; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro.

In certain embodiments, a compound of Formula I can include one or more of bonds A-E, and hence one to four additional carbons, with the appropriate valencies. In certain embodiments, bonds B, C, and/or D are only present when one or both of bonds A or E are present. For example, compounds of the invention can include, bond A, bonds A-B, bonds A-C, bonds A-D, bonds A-E, bonds B-E, bonds C-E, bonds D-E, bond D, or bonds A-B and D-E. In one embodiment, a compound of the invention includes bond E. In another embodiment, a compound of the invention includes bonds A-E. In a further embodiment, bonds A-D or B-E can form a five-membered ring.

Exemplary acridine and quinoline molecules of the instant compound include, but are not limited to,

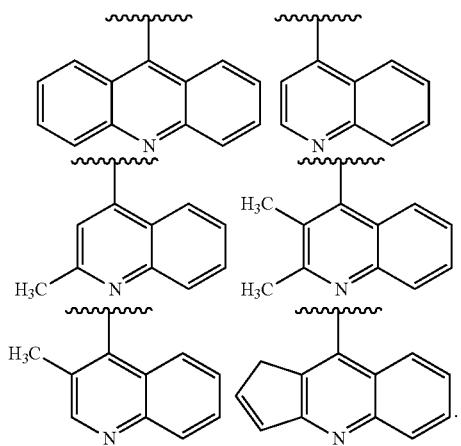

In addition to the above-disclosed molecules, it is contemplated that the one or more rings of acridine and quinoline molecules can be modified with one or more heteroatoms to produce modified bisintercalators.

Compounds of Formula I can be prepared and purified using any other suitable methodology routinely practiced in the art (see, Examples 1 and 2), and be analyzed for their pharmacological properties by routine methodologies. For example, kinetic solubility can be measured using a direct UV absorbance method or thermodynamic solubility can be measured. In addition, stability in gastrointestinal fluids can be determined by conventional methods (Asafu-Adjaye, et al. (2007) *J. Pharm. Biomed. Anal.* 43:1854-1859), e.g., 1 hour in simulated gastric fluid (pH 1.2, pepsin) at 37° C. and/or 3 hours in simulated intestinal fluid (pH 6.8, pancreatin). Furthermore, using the Parallel Artificial Membrane Permeability Assay (PAMPA)-blood-brain barrier (BBB) permeability assay (Di, et al. (2009) *J. Pharm. Sci.* 98:1980-1991) or B—P dialysis (Kalvass & Maurer (2002) *Biopharm. Drug Dispos.* 23(8):327-38), brain penetration can be assessed. Furthermore, lipophilicity can be estimated by partitioning between octanol and water using a shake flask method or pH metric method and permeability can be assessed using the Caco-2 cell layer method of PAMPA assay.

Wherein R of Formula I is a tetrazole or $CO_2H$, an internal salt can be prepared. Alternative, pharmaceutically acceptable salts of the present invention can be prepared by conventional methods. Salts encompassed within the term "pharmaceutically acceptable salts" refer to non-toxic salts of the compounds of this invention. Salts of the compounds of the present invention may include acid addition salts. In general, the salts are formed from pharmaceutically acceptable inorganic and organic acids, or bases, as well as quaternary ammonium salts. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, besylate, bicarbonate, bisulfate, bitartrate, borate, bromide, calcium edetate, camsylate, carbonate, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate/disalicylate, sodium, stearate, subacetate, succinate, sulfate, tannate, tartrate, teoclate, tosylate, triethiodide, trimethylammonium, and valerate salts.

More specific examples of suitable basic salts include benzathine, sodium, lysine, lithium, potassium, magnesium, aluminum, calcium, zinc, N,N'-dibenzylethylenediamine, chloroprocaine, chlorine, diethanolamine, ethylenediamine, N-methylglucamine, and procaine salts.

As used herein, the term "solvate" refers to a complex of variable stoichiometry formed by a solute (in this invention, a compound of Formula I, or a salt thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

Processes for preparing pharmaceutically acceptable salts and solvates of the compounds of Formula I are conventional in the art. See, for example, Burger's Medicinal Chemistry and Drug Discovery, 5th Edition, Volume 1: Principles and Practice.

The DNA binding activity and efficacy of the compounds of this invention can be demonstrated using any convention method. For example, thermal denaturation studies can be performed on calf thymus DNA (see, e.g., Fiel, et al. (1979) *Nucleic Acids Res.* 6(9):3093-118; Nakaike, et al. (1992) *Jpn. J. Cancer Res.* 83(4):402-9; Fairley, et al. (1993) *J. Med. Chem.* 36(12):1746-53). In addition, the compounds can be analyzed for their ability to exhibit cytotoxicity in suitable cell line or animal models of cancer. For example, the murine leukemia cell line, L1210, is used in in vitro assays (Jaycox, et al. (1987) *J. Heterocyclic. Chem.* 24:1405-1408), as well as in in vivo assays, wherein CD2F1 mice receive L1210 leukemia cells by intraperitoneal injection (Edanami, et al. (1984) *Cancer Chemother Pharmacol.* 13(1):22-6; Douzono, et al. (1995) *Jpn. J. Cancer Res.* 86(3):315-21). Similarly, the human mammary carcinoma MX-1 xenograft model is routinely used in the preclinical analysis of anti-tumor compounds in the treatment of breast cancer (Zhao, et al. (2008) *Bioconjug Chem.* 19(4):849-59; Wada, et al. (2007) *Anticancer Res.* 27:1431-5; Donawho, et al. (2007) *Clin Cancer Res.* 13:2728-37). In this model, NU/NU Swiss (nude) mice receive an intrarenal inoculation of MX-1 cells prior to or after treatment with the test compound. The human lung LX-1 xenograft model, wherein nude mice receive an intrarenal inoculation of LX-1 tumor cells, is also routinely used in the preclinical analysis of anti-tumor compounds (Masuda, et al. (2006) *J. Antibiot.* (*Tokyo*) 59(4):209-14). Similar models exist for the analysis of anti-tumor activity in prostate cancer (e.g., the TRAMP model, wherein transgenic mice develop spontaneous prostate cancer), skin cancer (e.g., the Mouse B16 Melanoma model), ovarian cancer (mouse ovarian carcinoma xenograft model; Davis, et al. (1993) *Cancer Research* 53:2087-2091) and kidney cancer (e.g., the murine renal cell carcinoma model (RENCA model)). Indeed, any suitable rodent or primate model can be used in the analysis of anti-tumor activity of the instant compounds. In each of these models, survival and/or tumor size is measured and the results are expressed as the measurement made in the treated group divided by the measurement made in the vehicle treated control group. Results of this analysis are expected to demonstrate that tumor size is decreased and or survival is increased in animals receiving treatment with a compound of the present invention.

Indeed, given the known antitumor activity bis-acridine or bis-quinoline intercalators, the compounds of the present invention find use in the treatment of cancer. In addition, the compounds of the present invention are contemplated as being more effective inhibitors of cancer cells than the antitumor bis-intercalators disclosed in the prior art because of their improved pharmacological properties. Accordingly, compounds of the present invention will be useful in treating subjects suffering from cancer, such as leukemia, colon cancer, glioma (including astrocytomas, ependymal tumors, glioblastoma multiforme, and primitive neuroectodermal tumors), breast cancer, kidney cancer, lung cancer and the like. Indeed, it is contemplated that any cancer conventionally treated with an anti-tumor acridine or quinoline will likewise be treated with a compound of the present invention.

Accordingly, the present invention also provides methods for treating cancer, wherein an effective amount of a compound of the present invention is administered to the subject in need of treatment so that growth of the cancer cells is inhibited or decreased and the signs or symptoms of the cancer are delayed, ameliorated, decreased or reversed. In this respect, "treatment" refers to both therapeutic treatment and prophylactic or preventative measures. As such, those in need of treatment include those already with the disorder as well as those prone to have the disorder (e.g., by genetic predisposition or exposure to carcinogenic agents). Subjects who can be treated in accordance with the present invention include mammals, such as humans, domestic and farm animals, and zoo, sports, or pet animals, e.g., dogs, horses, cats, cows, etc. Preferably, the mammal herein is human.

For the purposes of the present invention, the term "effective amount" means that amount of a drug or pharmaceutical agent that will elicit the biological or medical response of a tissue, system, animal, or human that is being sought, for instance, by a researcher or clinician. For use in therapy, effective amounts of a compound of Formula I, as well as salts or solvates thereof, may be administered as the raw chemical or optionally presented as a pharmaceutical composition.

Accordingly, the invention further provides pharmaceutical compositions (also referred to herein as "pharmaceutical formulations") that include effective amounts of compounds of the Formula I, or salts or solvates thereof, and one or more pharmaceutically acceptable excipients (including carriers and/or diluents). The carrier(s), diluent(s) or excipient(s) must be acceptable, in the sense of being compatible with the other ingredients of the formulation and not deleterious to the recipient of the pharmaceutical composition. In preparing the instant pharmaceutical formulation, a compound of the Formula I, or a salt or solvate thereof, is admixed with one or more pharmaceutically acceptable carriers, diluents or excipients.

Pharmaceutical formulations may be presented in unit dose forms containing a predetermined amount of active ingredient per unit dose. Such a unit may contain, as a non-limiting example, 0.5 mg to 1 g of a compound of the Formula I, depending on the compound, the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, topical (including buccal, sublingual or transdermal), vaginal, parenteral (including subcutaneous, intramuscular, intravenous or intradermal), by implantation, by intracavitary or intravesical instillation, intraocular, intraarterial, or intralesional route, or by application to mucous membranes, such as, that of the nose, throat, and/or bronchial tubes (i.e., inhalation). Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, alginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts and solvates thereof may be employed alone or in combination with other therapeutic agents. The compound(s) of Formula I and the other pharmaceutically active agent(s) may be administered together or separately and, when administered separately, administration may occur simultaneously or sequentially, in any order. The amounts of the compound(s) of Formula I and the other pharmaceutically active agent(s) and the relative timings of administration will be selected in order to achieve the desired combined therapeutic effect.

The invention is described in greater detail by the following non-limiting examples.

Example 1
Synthesis of Bis-Acridine Having a Modified Bis(4-Aminophenyl)Ether Tether
SCHEME 1
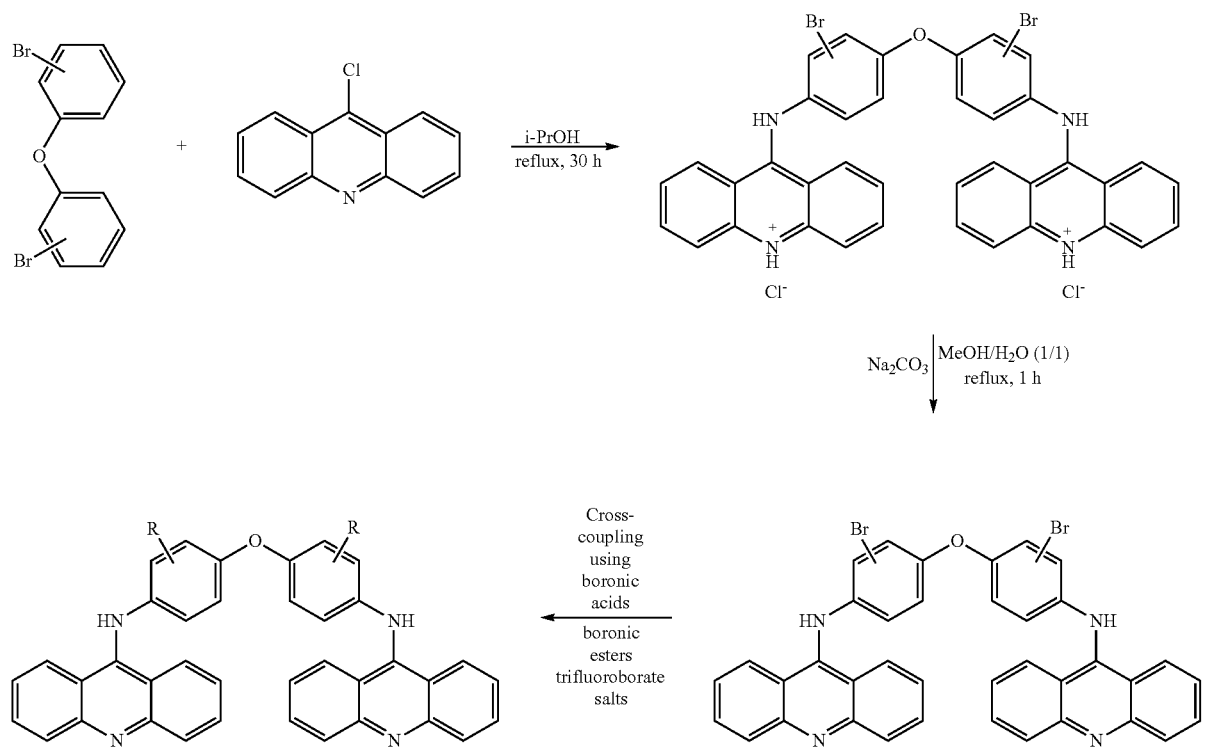
Example 2
Modifications to Bis-Acridine Intercalators
SCHEME 2
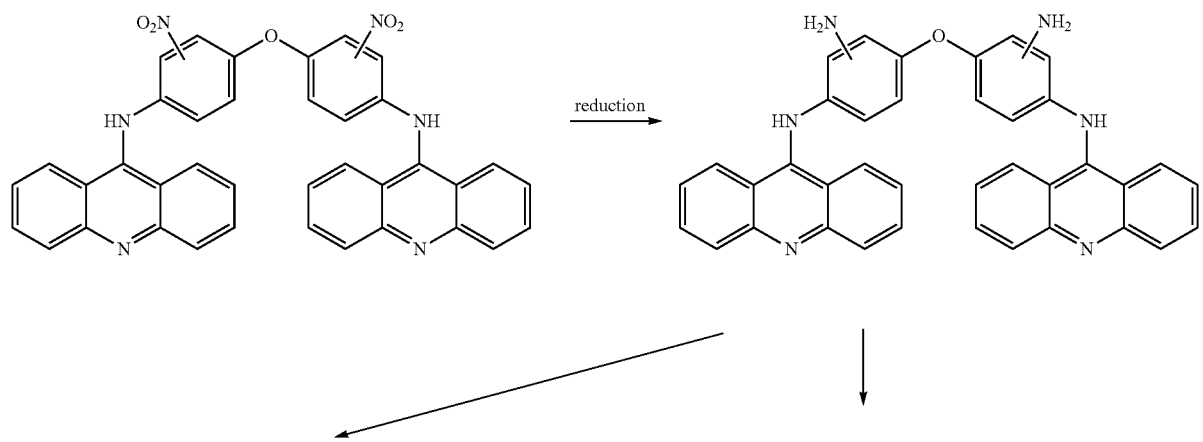

What is claimed is:

1. A method for inhibiting growth of a cancer cell comprising contacting a cancer cell with an effective amount of a compound of Formula I, or a pharmaceutically acceptable salt or solvate thereof,

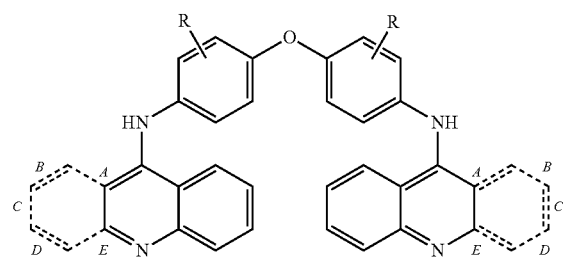

Formula I wherein,
dashed lines represent bonds that are independently present or absent; and
each R is independently an amide, amino, azido, nitro, hydroxyl, hydroxymethyl, carboxyl, cyano, sulfinyl, aryl, heteroaryl, alkenyl, alkyl, alkylene, cycloalkyl, cycloalkenyl, heterocycle, spirocycle, alkoxy, or halo group, so that growth of the cancer cell is inhibited.

2. A method for treating cancer comprising administering to a subject in need of treatment an effective amount of a pharmaceutical composition comprising a pharmaceutically acceptable carrier and a compound of Formula I, or a pharmaceutically acceptable salt or solvate thereof,

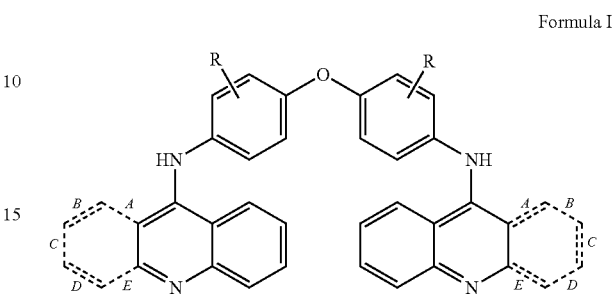

Formula I wherein,
dashed lines represent bonds that are independently present or absent; and
each R is independently an amide, amino, azido, nitro, hydroxyl, hydroxymethyl, carboxyl, cyano, sulfinyl, aryl, heteroaryl, alkenyl, alkyl, alkylene, cycloalkyl, cycloalkenyl, heterocycle, spirocycle, alkoxy, or halo group, thereby treating cancer in the subject.

* * * * *